United States Patent [19]

Baasner et al.

[11] Patent Number: 5,191,089
[45] Date of Patent: * Mar. 2, 1993

[54] HERBICIDAL 4-ALKOXY- AND 4-(SUBSTITUTED)AMINO-ARYLPYRROLI-NONE DERIVATIVES

[75] Inventors: Bernd Baasner, Bergisch Gladbach; Reiner Fischer, Monheim; Klaus Lürssen, Bergisch Gladbach; Hans-Joachim Santel, Leverkusen; Robert R. Schmidt, Bergisch Gladbach, all of Fed. Rep. of Germany

[73] Assignee: Bayer Aktiengesellschaft, Leverkusen, Fed. Rep. of Germany

[*] Notice: The portion of the term of this patent subsequent to Sep. 3, 2008 has been disclaimed.

[21] Appl. No.: 565,536

[22] Filed: Aug. 9, 1990

[30] Foreign Application Priority Data

Aug. 29, 1989 [DE] Fed. Rep. of Germany ....... 3928504

[51] Int. Cl.$^5$ ........................................... C07D 207/38
[52] U.S. Cl. ................................. 548/550; 504/283; 504/219; 504/225; 504/235; 504/287; 504/252; 504/239; 504/166; 504/167; 504/168
[58] Field of Search ........................................ 548/550

[56] References Cited

FOREIGN PATENT DOCUMENTS 0262399 4/1988 European Pat. Off. .
0026970 11/1964 Japan ................... 548/550
0004150 2/1967 Japan ................... 548/550

OTHER PUBLICATIONS

Liebigs Ann. Chem., 1985, pp. 1095–1098, R. Schmierer et al.; Cyclisierung von N-Acylalanin- und N-Acylglycinestern.

*Primary Examiner*—David B. Springer
*Attorney, Agent, or Firm*—Sprung Horn Kramer & Woods

[57] ABSTRACT

Herbicidal 4-alkoxy- and 4-(substituted)amino-arylpyrrolinone derivatives of the formula

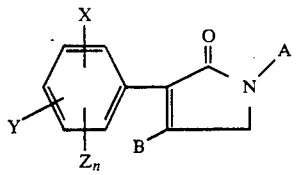

(I)

in which
X and Y independently of one another represent hydrogen, halogen, alkyl, alkoxy, halogenoalkyl or in each case unsubstituted or substituted aryloxy or arylthio,
Z represents halogen, alkyl or alkoxy,
n represents the number 0, 1, 2 or 3,
A represents in each case unsubstituted or in each case halogen-substituted alkyl, alkenyl, alkynyl, alkoxyalkyl, polyalkoxyalkyl or alkylthioalkyl, cycloalkyl which is optionally interrupted by hetero atoms, arylalkyl which is unsubstituted or substituted by halogen, alkyl, halogenoalkyl, alkoxy and/or nitro, unsubstituted aryl or aryl substituted by a member selected from the group consisting of halogen, alkyl, alkoxy, halogenoalkyl, halogenoalkoxy and phenoxy or phenylthio which are in each case unsubstituted or substituted by halogen, alkyl, alkoxy, halogenoalkyl and/or halogenoalkoxy,
B represents hydroxyl, alkoxy, halogenoalkoxy or cycloalkoxy, the cycloalkyl radical being unsubstituted or substituted by halogen and/or alkyl, or
B represents the group

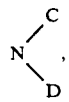

wherein
C and D independently of one another represent hydrogen, alkyl, alkenyl, alkoxyalkyl, alkylthioalkyl or polyalkoxyalkyl, cycloalkyl which is optionally interrupted by hetero atoms or in each case unsubstituted or substituted phenyl, phenylalkyl, phenoxyalkyl, hetaryl or hetarylalkyl, or
C and D together with the nitrogen atom to which they are bonded, form a 3- to 9-membered, optionally substituted ring which is optionally interrupted by the further hetero atoms, with the proviso that at least one radical X, Y or Z does not represent chlorine or methyl if B represents hydroxyl and A has a meaning other than optionally substituted aryl.

10 Claims, No Drawings

HERBICIDAL 4-ALKOXY- AND 4-(SUBSTITUTED)AMINO-ARYLPYRROLINONE DERIVATIVES

The invention relates to new 4-alkoxy- and 4-(substituted)amino-3-arylpyrrolinone derivatives, processes and new intermediate products for their preparation and their use as herbicides.

Pharmaceutical properties of 3-acyl-pyrrolidine-2,4-diones have already been described (S. Suzuki et al., Chem. Pharm. Bull. 15 1120 (1967)). N-Phenyl-pyrrolidine-2,4-diones have furthermore have synthesized by R. Schmierer and H. Mildenberger, Liebigs Ann. Chem. 1985 1095. No biological activity of these compounds has been described.

Compounds of similar structure (3-aryl-pyrrolidine-2,4-diones) are disclosed in EP-A 0,262,399, but no herbicidal activity of these compounds has been disclosed.

3-Arylpyrrolidine-2,4-dione derivatives which have an insecticidal, acaricidal and herbicidal action and which can contain hydroxyl in the 4-position of the pyrrolinone are furthermore described in German Patent Application P 3 900 301.9 of Jan. 7, 1989, corresponding to U.S. application Ser. No. 460,208, filed Jan. 2, 1990, now pending. Compounds mentioned by name in the above-mentioned application are excluded from the scope of protection of the present application by means of disclaimers.

New 4-alkoxy- and 4-(substituted)amino-3-arylpyrrolinone derivatives of the general formula (I)

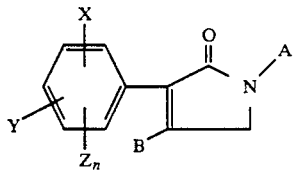

in which
X and Y independently of one another represent hydrogen, halogen, alkyl, alkoxy, halogenoalkyl or in each case unsubstituted or substituted aryloxy or arylthio,
Z represents halogen, alkyl or alkoxy,
n represents the number 0, 1, 2 or 3,
A represents in each case unsubstituted or in each case halogen-substituted alkyl, alkenyl, alkynyl, alkoxyalkyl, polyalkoxyalkyl or alkylthioalkyl, cycloalkyl which is optionally interrupted by hetero atoms, arylalkyl which is unsubstituted or substituted by halogen, alkyl, halogenoalkyl, alkoxy and/or nitro, or unsubstituted or substituted aryl, possible substituents being halogen, alkyl, alkoxy, halogenoalkyl, halogenoalkoxy or phenoxy or phenylthio which are in each case unsubstituted or substituted by halogen, alkyl, alkoxy, halogenoalkyl and/or halogenoalkoxy,
B represents hydroxyl, alkoxy, halogenoalkoxy or cycloalkoxy, the cycloalkyl radical being unsubstituted or substituted by halogen and/or alkyl, or
B represents the group

wherein
C and D independently of one another represent hydrogen, alkyl, alkenyl, alkoxyalkyl, alkylthioalkyl or polyalkoxyalkyl, cycloalkyl which is optionally interrupted by hetero atoms or in each case unsubstituted or substituted phenyl, phenylalkyl, phenoxyalkyl, hetaryl or hetarylalkyl, or
C and D together with the nitrogen atom to which they are bonded, form a 3- to 9-membered, optionally substituted ring which is optionally interrupted by further hetero atoms,
with the proviso that at least one radical X, Y or Z does not represent chlorine or methyl if B represents hydroxyl and A has a meaning other than optionally substituted aryl, have now been found.

The aliphatic carbon chains, such as, for example, alkyl, halogenoalkyl, arylalkyl or phenoxyalkyl, are in each case straight-chain or branched.

In substituted systems, such as, for example, substituted alkyl, alkenyl, cycloalkyl or aryl, the substitution can in each case be by one or more identical or different substituents. Aromatic systems are preferably substituted by one to five, in particular one to three substituents, and cyclic systems are preferably substituted by one to eight, in particular one to five substituents.

It has furthermore been found that the compounds of the formula (I), in which a) B represents hydroxyl and in which the radicals A, X, Y and $Z_n$ have the abovementioned meanings, are obtained by a process in which N-acylamino acid esters of the formula (II)

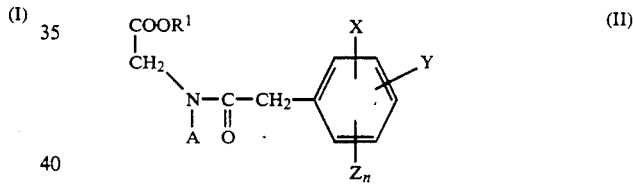

in which
A, X, Y, Z and n have the abovementioned meanings and $R^1$ represents alkyl, in particular methyl or ethyl, are subjected to intramolecular condensation in the presence of a diluent and in the presence of a base, or b) compounds of the formula (I) in which B represents alkoxy, halogenoalkoxy or cycloalkoxy, the cycloalkyl radical being unsubstituted or substituted by halogen and/or alkyl, and A, X, Y, Z and n have the abovementioned meanings, are obtained by a process in which compounds of the formula (I) in which B represents hydroxyl, are reacted with alkylating reagents of the formula (III)

$$R^2-X^1 \qquad (III)$$

in which
$R^2$ represents alkyl, halogenoalkyl or cycloalkyl, the cycloalkyl radical being unsubstituted or substituted by halogen and/or alkyl, and
$X^1$ represents halogen or another leaving group customary for alkylating reagents, if appropriate in the presence of a diluent and if appropriate in the presence of an acid-binding agent, or c) compounds of the formula (I) in which
B represents

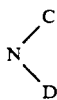

and

A, C, D, X, Y, Z and n have the abovementioned meanings, are obtained by a process in which compounds of the formula (I) in which B represents hydroxyl are reacted with amines of the formula (IV)

 (IV)

in which

C and D have the abovementioned meanings, is appropriate in the presence of a diluent and if appropriate in the presence of a dehydrating agent.

Finally, it has been found that the new 4-alkoxy-and 4-(substituted)amino-3-arylpyrrolinones of the general formula (I) have herbicidal properties.

Surprisingly, the 4-alkoxy- and 4-(substituted)-amino-3-arylpyrrolinones of the general formula (I) according to the invention exhibit an outstanding herbicidal activity and at the same time an excellent tolerability towards important crop plants.

Preferred compounds of the formula (I) are those in which

X and Y independently of one another represent hydrogen, fluorine, chlorine, bromine, iodine, $C_1$-$C_6$-alkyl, $C_1$-$C_6$-alkoxy, halogeno-$C_1$-$C_4$-alkyl or phenoxy or phenylthio which are in each case unsubstituted or substituted by one to five identical or different substituents, the substituents selected for the phenyl being: fluorine, chlorine, bromine, iodine, $C_1$-$C_4$-alkyl, $C_1$-$C_4$-alkoxy and halogen-$C_1$-$C_4$-alkyl, Z represents fluorine, chlorine, bromine, iodine, $C_1$-$C_6$-alkyl or $C_1$-$C_6$-alkoxy, n represents the number 0, 1, 2 or 3, A represents in each case unsubstituted or in each case halogen-substituted $C_1$-$C_{12}$-alkyl, $C_3$-$C_8$-alkenyl, $C_3$-$C_8$-alkinyl, $C_1$-$C_{10}$-alkoxy-$C_2$-$C_8$-alkyl, $C_1$-$C_8$-polyalkoxy-$C_1$-$C_8$-alkyl or $C_1$-$C_{10}$-alkylthio-$C_1$-$C_8$-alkyl, or represents cycloalkyl which has 3 to 8 ring atoms and can be interrupted by oxygen, nitrogen and/or sulphur, or A represents phenyl-$C_1$-$C_6$-alkyl, phenyl or naphthyl, in each case unsubstituted or substituted in the phenyl part by one to five identical or different substituents, the substituents selected in each case being chosen from: fluorine, chlorine, bromine, iodine, $C_1$-$C_6$-alkyl, $C_1$-$C_6$-alkoxy halogeno-$C_1$-$C_6$-alkoxy or phenoxy or phenylthio which are in each case unsubstituted or substituted by one to five identical or different substituents from the group comprising fluorine, chlorine, bromine, iodine, $C_1$-$C_4$-alkyl, $C_1$-$C_4$-alkoxy, halogeno-$C_1$-$C_4$-alkyl and halogeno-$C_1$-$C_4$-alkoxy, B represents hydroxyl, $C_1$-$C_{10}$-alkoxy, halogeno-$C_1$-$C_{10}$-alkoxy or cycloalkoxy having 3 to 7 ring atoms, the cycloalkyl radical being unsubstituted or substituted by one to five identical or different substituents from the group comprising fluorine, chlorine, bromine and $C_1$-$C_4$-alkyl, or B represents the group

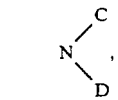

wherein

C and D independently of one another represent hydrogen, $C_1$-$C_{10}$-alkyl, $C_3$-$C_{10}$-alkenyl, $C_1$-$C_8$-alkoxy-$C_1$-$C_8$-alkyl, $C_1$-$C_8$-alkylthio-$C_1$-$C_8$-alkyl, $C_1$-$C_8$-polyalkoxy-$C_1$-$C_8$-alkyl, cycloalkyl having 3 to 8 ring atoms, which can be interrupted by one, two or three identical or different oxygen, nitrogen and sulphur atoms, or phenyl, phenyl-$C_1$-$C_6$-alkyl, phenoxy-$C_1$-$C_6$-alkyl, hetaryl or hetaryl-$C_1$-$C_6$-alkyl, having in each case 5 or 6 ring atoms and containing 1 or 2 identical or different oxygen, nitrogen and sulphur atoms in the ring, which are in each case unsubstituted or substituted by one to five identical or different substituents, or C and D, together with the nitrogen atom to which they are bonded, form a 3- to 8-membered ring which can contain one or two double bonds, can contain one or two further identical or different oxygen, sulphur or nitrogen atoms and can be substituted by one to five identical or different substituents from the group comprising $C_1$-$C_4$-alkyl and $C_1$-$C_4$-alkylcarbonyl, with the proviso that at least one radical X, Y or Z does not represent chlorine or methyl if B represents hydroxyl and A has a meaning other than optionally substituted phenyl or naphthyl.

A particularly preferred group of compounds of the formula (I) is that in which

B represents hydroxyl, methoxy, ethoxy, n- or iso-propoxy, n-, iso-, sec.- or tert.-butoxy, halogeno-$C_1$-$C_4$-alkoxy containing fluorine and/or chlorine atoms, or cycloalkoxy having 3 to 6 ring atoms, the cycloalkyl radical being unsubstituted or substituted by one to three identical or different substituents from the group comprising fluorine, chlorine, methyl and ethyl, X represents hydrogen, fluorine, chlorine, methyl, ethyl, n- or iso-propyl, methoxy, ethoxy, n- or i-propoxy, halogenomethyl, containing 1, 2 or 3 fluorine and/or chlorine atoms, halogenoethyl containing 1 to 5, in particular 1 to 3, fluorine and/or chlorine atoms, or phenoxy or phenylthio which are in each case unsubstituted or substituted by one to five, in particular one to three, identical or different substituents, the substituents selected for the phenyl being: fluorine, chlorine, bromine, methyl, ethyl, n- or iso-propyl, methoxy, ethoxy, n- or iso-propoxy and trifluoromethyl, Y represents hydrogen, fluorine, chlorine, methyl, ethyl, methoxy, ethoxy or trifluoromethyl, Z represents fluorine or chlorine, n represents 0, 1, 2 or 3 and A represents methyl, ethyl, in each case straight-chain or branched propyl, butyl, pentyl, hexyl, heptyl, octyl, nonyl or decyl, halogeno-$C_1$-$C_6$-alkyl, $C_3$-$C_6$-alkenyl, $C_3$-$C_6$-alkynyl, $C_1$-$C_4$-alkoxy-$C_1$-$C_4$-alkyl or $C_1$-$C_4$-alkylthio-$C_1$-$C_4$-alkyl, or represents cycloalkyl which has 3 to 6 ring atoms and can be interrupted by oxygen, nitrogen or sulphur, or A represents phenyl, benzyl or phenethyl which are in each case unsubstituted or substituted by one to five, in particular one to three, identical or different substituents, the substituents selected in each case being: fluorine, chlorine, methyl, ethyl, n- or iso-propoyl, methoxy, ethoxy, trifluoromethyl, trifluoromethoxy or phenoxy or phenylthio, which are in each case unsubstituted or substituted by one to three identical or different substituents from the group comprising fluorine, chlorine, methyl, methoxy, trifluoromethyl and trifluoromethoxy, with the proviso that at least one radical X, Y or Z does not represent chlorine or methyl if B represents hydroxyl and A has a meaning other than optionally substituted phenyl.

A particularly preferred group of compounds of the formula (I) is also that in which B represents the group

wherein

C represents hydrogen, methyl, ethyl or n- or iso-propyl and

D represents methyl, ethyl, n- or iso-propyl, n-, iso- sec.- or tert.-butyl, allyl, propargyl, methoxymethyl, methoxyethyl, ethoxymethyl, ethoxyethyl, methylthiomethyl, methylthioethyl, ethylthiomethyl, ethylthioethyl, cyclopropyl, cyclopentyl, cyclohexyl or phenyl, benzyl or phenethyl, which are in each case unsubstituted or substituted by one to five, in particular one to three, identical or different substituents from the group consisting fluorine, chlorine, methyl, ethyl and trifluoromethyl, or represents pyridyl or pyrimidyl, or C and D, together with the nitrogen atom to which they are bonded, form a 5- or 6-membered ring which can contain one or two double bonds or can contain a further nitrogen, oxygen or sulphur atom and can be substituted by one to three identical or different substituents from the group comprising methyl, ethyl, methylcarbonyl and ethylcarbonyl, X represents hydrogen, fluorine, chlorine, methyl, ethyl, n- or iso-propyl, methoxy, ethoxy, n- or i-propoxy, halogenomethyl, which contains 1, 2 or 3 fluorine and/or chlorine atoms, halogenoethyl, which contains 1 to 5, in particular 1 to 3, fluorine and/or chlorine atoms, or phenoxy or phenylthio which are in each case unsubstituted or substituted by one to five, in particular one to three, identical or different substituents, the substituents selected for the phenyl being: fluorine, chlorine, bromine, methyl, ethyl, n- or iso-propyl, methoxy, ethoxy, n- or iso-propoxy and trifluoromethyl, Y represents hydrogen, fluorine, chlorine, methyl, ethyl, methoxy, ethoxy or trifluoromethyl, Z represents fluorine or chlorine, n represents 0, 1, 2 or 3 and A represents methyl, ethyl, in each case straight-chain or branched propyl, butyl, pentyl, hexyl, heptyl, octyl, nonyl or decyl, halogeno-$C_1$-$C_6$-alkyl, $C_3$-$C_6$-alkenyl, $C_3$-$C_6$-alkynyl, $C_1$-$C_4$-alkoxy-$C_1$-$C_4$-alkyl or $C_1$-$C_4$-alkylthio-$C_1$-$C_4$-alkyl, or represents cycloalkyl which has 3 to 6 ring atoms and can be interrupted by oxygen, nitrogen or sulphur, or A represents phenyl, benzyl or phenethyl, in each case unsubstituted or substituted by one to five, in particular one to three, identical or different substituents, the substituents selected in each case being: fluorine, chlorine, methyl, ethyl, n- or iso-propyl, methoxy, ethoxy, trifluoromethyl, trifluoromethoxy or phenoxy or phenylthio, which are in each case unsubstituted or substituted by one to three identical or different substituents from the group comprising fluorine, chlorine, methyl, methoxy, trifluoromethyl and trifluoromethoxy.

An especially preferred group of compounds is that in which

B represents hydroxy, methoxy, ethoxy or n- or iso-propoxy,

X represents fluorine, chlorine or trifluoromethyl in the meta-position of the phenyl ring, or represents phenyl or phenoxy, which are in each case unsubstituted or substituted by one to three identical or different substituents, the substituents selected being: fluorine, chlorine, methyl and trifluoromethyl, Y represents hydrogen, fluorine or chlorine, n represents 0 and A represents methyl, ethyl, n-propyl, iso-propyl, n-, iso-, sec.- or tert.-butyl, in each case straight-chain or branched pentyl, hexyl, heptyl or octyl, halogen-$C_1$-$C_3$-alkyl, allyl, propargyl, methoxymethyl, methoxyethyl, ethoxymethyl, ethoxyethyl, cyclopropyl, cyclopentyl, cyclohexyl, or phenyl or benzyl, which are in each case unsubstituted or substituted by one to three identical or different substituents from the group comprising fluorine, chlorine, trifluoromethyl, phenoxy and 4-trifluoromethyl-phenoxy.

An especially preferred group of compounds of the formula (I) is also that in which B represents the group

wherein

C represents hydrogen and

D represents methyl, ethyl, n- or iso-propyl, n-, iso-, sec.- or tert.-butyl or phenyl, which is unsubstituted or substituted by one to three identical or different substituents from the group comprising fluorine, chlorine and trifluoromethyl, or C and D, together with the nitrogen to which they are bonded, represent a heterocyclic radical of the formula:

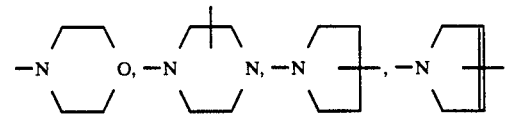

which is optionally substituted by one to three identical or different substituents from the group comprising methyl, ethyl, methylcarbonyl and ethylcarbonyl, X represents fluorine, chlorine or trifluoromethyl in the meta-position of the phenyl ring, or represents phenyl or phenoxy, in each case unsubstituted or substituted by one to three identical or different substituents, the substituents selected being: fluorine, chlorine, methyl and trifluoromethyl, Y represents hydrogen, fluorine or chlorine, n represents 0 and A represents methyl, ethyl, n-propyl, isopropyl, n-, iso-, sec.- or tert.-butyl, in each case straight-chain or branched pentyl, hexyl, heptyl or octyl, halogen-$C_1$-$C_3$-alkyl, allyl, propargyl, methoxymethyl, methoxyethyl, ethoxymethyl, ethoxyethyl, cyclopropyl, cyclopentyl, cyclohexyl, or phenyl or benzyl which are in each case unsubstituted or substituted by one to three identical or different substituents from the group comprising fluorine, chlorine, trifluoromethyl, phenoxy and 4-trifluoromethylphenoxy.

In all the abovementioned ranges of definitions, the meaning of X as trifluoromethyl in the meta-position of the phenyl ring is to be singled out in particular.

If ethyl N-(3-trifluoromethylphenylacetyl)-N-methyl-aminoacetate is used in accordance with the general preparation process (a), the course of the process according to the invention is represented by the following equation:

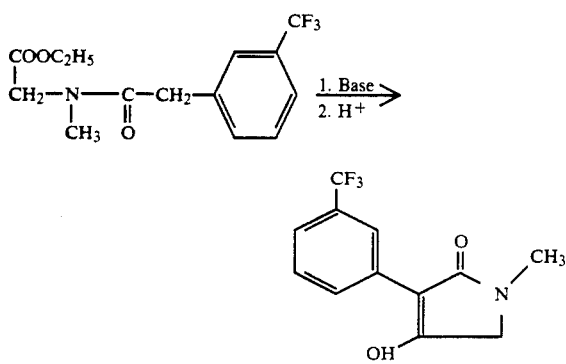

If 3-(3-trifluoromethylphenyl)-1-tert.-butyl-pyrrolidine-2,4-dione and methyl p-toluenesulphonate are used as starting substances in accordance with the general preparation process (b), the course of the process according to the invention is represented by the following equation:

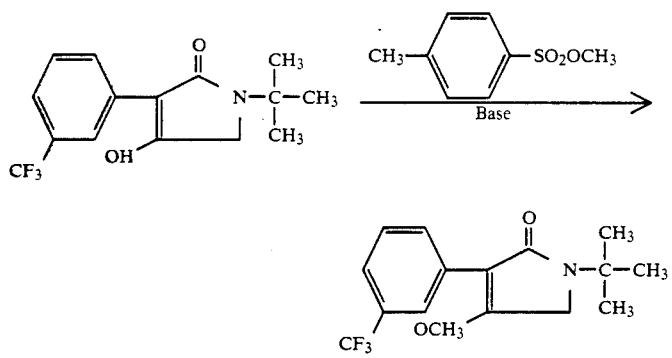

If 3-(3-trifluoromethylphenyl)-1-isopropylpyrrolidine-2,4-dione and methylamine are used as starting substances in accordance with the general preparation process (c), the course of the process according to the invention is represented by the following equation:

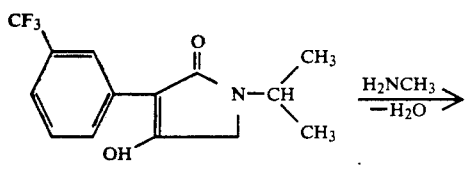

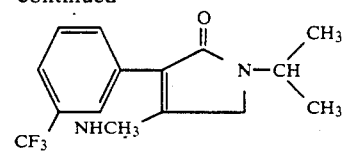

The compounds of the formula (II) required as starting substances for carrying out process (a) according to the invention are known in some cases or can be prepared in a simple manner by methods which are known in principle.

Thus, for example, N-acylamino acid esters of the formula (II) are obtained by a process in which acylamino acid esters of the formula (V)

in which

R$^1$ represents hydrogen or alkyl, in particular methyl or ethyl, and

A has the abovementioned meaning, are acylated with phenylacetyl halides of the formula (VI)

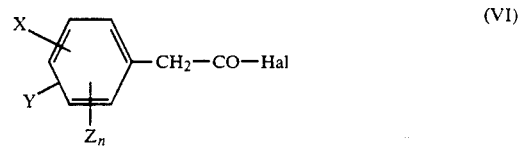

in which

Hal represents halogen, in particular fluorine, chlorine or bromine, and

X, Y, Z and n have the abovementioned meanings, in the customary manner (compare Chem. Rev. 52 (1953) 237–416 and Organicum, 9th edition 446 (1970) VEB Deutscher Verlag der Wissenschaften)

or by a process in which N-acylamino acids of the formula (II) in which R$^1$ represents hydrogen are esterified in the customary manner (compare Chem. Ind. (London) 1568 (1968)).

Compounds of the formula (II) in which R$^1$ represents hydrogen can also be prepared, for example, from phenylacetyl halides of the formula (VI) and amino acids.

Compounds of the formula (V) are obtainable by processes which are known from the literature from α-halogenocarboxylic acids or esters and amines (Advanced Organic Chemistry, J. March page 377, McGraw-Hill Inc. (1977)).

The phenylacetyl halides of the formula (VI) are known compounds of organic chemistry.

The following compounds of the formula (II) may be mentioned as examples:

1. Ethyl N-(3-trifluoromethylphenylacetyl)-N-isopopylaminoacetate
2. Ethyl N-(3-trifluoromethylphenylacetyl)-N-(1,1,3,3-tetramethyl)butylaminoacetate
3. Ethyl N-(3-trifluoromethylphenylacetyl)-N-2,4,6-trimethylphenylaminoacetate
4. Ethyl N-(3-trifluoromethylphenylacetyl)-N-cyclobutylaminoacetate
5. Ethyl N-(3-trifluoromethylphenylacetyl)-N-cyclopentylaminoacetate
6. Ethyl N-(3-trifluoromethylphenylacetyl)-N-cyclohexylaminoacetate
7. Ethyl N-(3-trifluoromethylphenylacetyl)-N-(2-methoxyethyl)aminoacetate
8. Ethyl N-(3-trifluoromethylphenylacetyl)-N-(1-trifluoromethylethyl)aminoacetate
9. Ethyl N-(3-trifluoromethylphenylacetyl)-N-phenylaminoacetate
10. Ethyl N-(3-trifluoromethylphenylacetyl)-N-2-chlorophenylaminoacetate
11. Ethyl N-(3-trifluoromethylphenylacetyl)-N-4-chlorophenylaminoacetate
12. Ethyl N-(3-trifluoromethylphenylacetyl)-N-2,4-dichlorophenylaminoacetate
13. Ethyl N-(3-trifluoromethylphenylacetyl)-N-2,6-dichlorophenylaminoacetate
14. Ethyl N-(3-trifluoromethylphenylacetyl)-N-4-trifluoromethylphenylaminoacetate
15. Ethyl N-(3-trifluoromethylphenylacetyl)-N-2-chloro-5-trifluoromethylphenylaminoacetate
16. Ethyl N-(3-trifluoromethylphenylacetyl)-N-5-trifluoromethylphenylaminoacetate
17. Ethyl N-(3-trifluoromethylphenylacetyl)-N-2-fluorophenylaminoacetate
18. Ethyl N-(3-trifluoromethylphenylacetyl)-N-4-fluorophenylaminoacetate
19. Ethyl N-(3-trifluoromethylphenylacetyl)-N-2,6-difluorophenylaminoacetate
20. Ethyl N-(3-trifluoromethylphenylacetyl)-N-2,4-difluorophenylaminoacetate
21. Ethyl N-(3-trifluoromethylphenylacetyl)-N-2,2-dimethylpropylaminoacetate
22. Ethyl N-(3-trifluoromethylphenylacetyl)-N-1,2,2-trimethylpropylaminoacetate
23. Ethyl N-(3-trifluoromethylphenylacetyl)-N-benzylaminoacetate
24. Ethyl N-(3-trifluoromethylphenyl)-aminoacetate
25. Ethyl N-phenylacetyl-N-cyclopropylaminoacetate
26. Ethyl N-(3-trifluoromethylphenylacetyl)-N-1,2-dimethylpropylaminoacetate
27. Ethyl N-(3-trifluoromethylphenylacetyl)-N-3,4-dichlorophenylaminoacetate
28. Ethyl N-(2,4,6-trichloro-3-fluoro-5-phenoxyphenylacetyl)-N-phenylaminoacetate
29. Ethyl N-(4-trifluoromethyl-2-chloro-6-fluorophenylacetyl)-N-phenylaminoacetate
30. Ethyl N-(3-trifluoromethylphenylacetyl)-N-3-chlorophenylaminoacetate
31. Ethyl N-phenylacetyl-N-phenylaminoacetate
32. Ethyl N-phenylacetyl-N-2,4-difluorophenylaminoacetate
33. Ethyl N-(2-(2,4-dimethylphenoxy)phenylacetyl)-N-phenylaminoacetate
34. Ethyl N-(2-phenoxy-phenylacetyl)-N-phenylaminoacetate
35. Ethyl N-(3-trifluoromethylphenylacetyl)-N-4-phenoxyphenyl)aminoacetate
36. Ethyl N-(3-trifluoromethylphenylacetyl)-N-4-(4-trifluoromethylphenoxy)phenylaminoacetate
37. Ethyl N-(4-trifluoromethyl-2-chloro-6-fluorophenylacetyl)-N-phenylaminoacetate
38. Ethyl N-Phenylacetyl-N-2-chlorphenyl-aminoacetate
39. Ethyl N-(2,4-Difluorphenylacetyl)-N-3-trifluormethylphenyl-aminoacetate
40. Ethyl N-(3-Trifluormethylphenylacetyl)-N-(3-trifluormethylphenyl-4-phenoxyphenyl)-aminoacetate
41. Ethyl N-phenylacetyl-N-3-chlorophenylaminoacetate
42. Ethyl N-phenylacetyl-N-4-chlorophenylaminoacetate
43. Ethyl N-phenylacetyl-N-3,4-dichlorophenylaminoacetate
44. Ethyl N-(3-trifluoromethylphenylacetyl)-N-methylaminoacetate
45. Ethyl N-(3-trifluoromethylphenylacetyl)-N-tert.-butylaminoacetate
46. Ethyl N-(3-phenoxy-phenylacetyl)-N-phenylaminoacetate
47. Ethyl N-(3-phenoxy-phenylacetyl)-N-(3-trifluoromethylphenyl)-aminoacetate
48. Ethyl N-(4-phenoxy-phenylacetyl)-N-phenylaminoacetate
49. Ethyl N-(4-phenoxy-phenylacetyl)-N-(trifluoromethylphenyl)-aminoacetate
50. Ethyl N-(3-trifluromethylphenylacetyl)-N-(4-cyclohexylphenyl)-aminoacetate
51. Ethyl N-(2-phenoxy-phenylacetyl)-N-(3-trifluoromethylphenyl)-aminoacetate
52. Ethyl N-phenylacetyl-N-(4-fluorophenyl)-aminoacetate
53. Ethyl N-(3-trifluoromethylphenylacetyl)-N-(2-methylphenyl)-aminoacetate
54. Ethyl N-(3-trifluoromethylphenylacetyl)-N-(3-methylphenyl)-aminoacetate
55. Ethyl N-(3-trifluoromethylphenylacetyl)-N-(4-methylphenyl)-aminoacetate
56. Ethyl N-(4-methylphenylacetyl)-N-(4-fluorophenyl)-aminoacetate
57. Ethyl N-(2-methylphenylacetyl)-N-(4-fluorophenyl)-aminoacetate
58. Ethyl N-(2-methylphenylacetyl)-N-(3-trifluoromethylphenyl)-aminoacetate
59. Ethyl N-(2-fluorophenylacetyl)-N-(2-methylphenyl)-aminoacetate
60. Ethyl N-(4-fluorophenylacetyl)-N-(2-methylphenyl)-aminoacetate
61. Ethyl N-(2-fluorophenylacetyl)-N-(4-methylphenyl)-aminoacetate
62. Ethyl N-(2-fluorophenylacetyl)-N-(3-trifluoromethylphenyl)-aminoacetate
63. Ethyl N-(4-fluorophenylacetyl)-N-phenylaminoacetate
64. Ethyl N-(4-fluorophenylacetyl)-N-(3-chlorophenyl)-aminoacetate
65. Ethyl N-(2,4-difluorophenylacetyl)-N-(4-fluorophenyl)-aminoacetate
66. Ethyl N-(2,4-difluorophenylacetyl)-N-(2-methylphenyl)-aminoacetate 67. Ethyl-N-(2,4-difluorophenylacetyl)-N-(3-methylphenyl)-aminoacetate
68. Ethyl N-(2,4-difluorophenylacetyl)-N-(4-methylphenyl)-aminoacetate
69. Ethyl N-(2,4-difluorophenylacetyl)-N-(2,4-difluorophenyl)-aminoacetate
70. Ethyl N-(3-fluorophenylacetyl)-N-(3-methylphenyl)-aminoacetate
71. Ethyl N-(3-fluorophenylacetyl)-N-(4-methylphenyl)-aminoacetate
72. Ethyl N-(3-fluorophenylacetyl)-N-(3-fluorophenyl)-aminoacetate
73. Ethyl N-(2-methylphenylacetyl)-N-phenylaminoacetate The compounds of the formula (I) where B=hydroxyl which are required as starting substances for carrying out process (b) and (c) according to the invention are compounds according to the invention and are obtainable by process (a).

The alkylating reagents of the formula (III) furthermore required as starting substances for carrying out process (b) according to the invention are known compounds or organic chemistry.

In formula (III), $R^2$ preferably represents $C_1$-$C_{10}$-alkyl, halogeno-$C_1$-$C_{10}$-alkyl or cycloalkyl having 3 to 7 ring atoms, the cycloalkyl radical being unsubstituted or substituted by one to five identical or different substituents from the group comprising fluorine, chlorine, bromine and $C_1$-$C_4$-alkyl. $R^2$ particularly preferably represents methyl, ethyl, propyl or iso-propyl.

In formula (III), $X^1$ preferably represents chlorine, bromine or iodine, $C_1$-$C_4$-alkylsulphonyloxy, $C_1$-$C_4$-alkoxysulphonyloxy or p-toluenesulphonyloxy, such as, for example, methanesulphonyloxy, methoxysulphonyloxy or ethoxysulphonyloxy.

The alkylating reagents of the formula (III) are known compounds of organic chemistry.

The amines of the formula (IV) required as starting substances for carrying out process (c) according to the invention are generally known compounds or can be prepared by known methods (compare Houben-Weyl, Methoden der Organischen Chemie, Volume XI/1, Georg-Thieme-Verlag, Stuttgart 1957).

Process (a) is characterized in that compounds of the formula (II) are subjected to an intramolecular condensation in the presence of bases.

Diluents which can be employed in process (a) according to the invention are all the customary inert organic solvents. Solvents which can preferably be used are hydrocarbons, such as toluene and xylene, and furthermore ethers, such as dibutylether, tetrahydrofuran, dioxane, glycoldimethylether and diglycoldimethylether, and also polar solvents, such as dimethylsulphoxide, sulpholane, dimethylformamide and N-methylpyrrolidone.

Deprotonating agents which can be employed in carrying out process (a) according to the invention are all the customary proton acceptors. Proton acceptors which can preferably be used are alkali metal oxides, hydroxides and carbonates and alkaline earth metal oxides, hydroxides and carbonates, such as sodium hydroxide, potassium hydroxide, magnesium oxide, calcium oxide, sodium carbonate, potassium carbonate and calcium carbonate, which can also be employed in the presence of phase transfer catalysts, such as, for example, triethylbenzylammonium chloride, tetrabutylammonium bromide, Adogen 464 methyltrialkyl ($C_8$-$C_{10}$) ammonium chloride or TDA tris-(methoxyethoxyethyl)-amine. Alkali metal amides and hydrides and alkaline earth metal amides and hydrides, such as sodium amide, sodium hydride and calcium hydride, and furthermore also alkali metal alcoholates, such as sodium methylate, sodium methylate and potassium tert.-butylate, can furthermore be employed.

The reaction temperature can be varied within a substantial range in carrying out process (a) according to the invention. The reaction is in general carried out at temperatures between 0° C. and 250° C., preferably between 50° C. and 150° C.

Process (a) according to the invention is in general carried out under normal pressure.

In carrying out process (a) according to the invention, the reaction components of the formulae (II) and the deprotonating bases are in general employed in approximately equimolar amounts. However, it is also possible for one or other of the components to be used in a relatively large excess (up to 3 molar).

Possible diluents for carrying out process (b) according to the invention are inert organic solvents. Solvents which are preferably used are aliphatic, alicyclic or aromatic, optionally halogenated hydrocarbons, such as, for example, benzine, benzene, toluene, xylene, pentane, hexane, heptane, cyclohexane, petroleum ether, ligroin, methylene chloride, chloroform, carbon tetrachloride, chlorobenzene or dichlorobenzene, ethers, such as diethyl ether, diisopropyl ether, dioxane, tetrahydrofuran or ethylene glycol diethyl or dimethyl ether, ketones, such as acetone, butanone, methylisopropyl ketone or methylisobutyl ketone, esters, such as ethyl acetate, acids, such as acetic acid, nitriles, such as acetonitrile or propionitrile, and amides, such as dimethylformamide, dimethylacetamide, N-methyl-pyrrolidone or hexamethylphosphoric acid triamide. If compounds of the formula (III) in liquid form are used as reaction partners, it is also possible for these simultaneously to be employed in a corresponding excess as the diluent.

Possible acid-binding agents for carrying out process (b) according to the invention are all the inorganic and organic bases which can usually be employed. Bases which are preferably used are alkali metal hydrides, hydroxides, amides, carbonates or bicarbonates, such as, for example, sodium hydride, sodium amide, sodium hydroxide, sodium carbonate or sodium bicarbonate, or tertiary amines, such as, for example, triethylamine, N,N-dimethylaniline, pyridine, 4-(N,N-dimethylamino)-pyridine, diazabicyclooctane (DABCO), diazabicyclononene (DBN) or diazabicycloundecene (DBU).

The reaction temperatures can be varied within a substantial range in carrying out process (b) according to the invention. The reaction is in general carried out between −20° C. and +150° C., preferably between 0° C. and +100° C.

For carrying out process (b) according to the invention, in general in each case 1 to 20 moles, preferably in each case 1 to 15 moles, of alkylating agent of the formula (III) and if appropriate 1 to 3 moles, preferably 1 to 2 moles, of acid-binding agent are employed per mole of compound of the formula (I) in which B represents hydroxyl. The reaction is carried out and the reaction products of the formula (I) are worked up and isolated by customary methods (compare also the preparation examples).

Preferred possible diluents for carrying out process (c) according to the invention are inert organic solvents.

These include, in particular, aliphatic, alicyclic or aromatic, optionally halogenated hydrocarbons, such as, for example, benzine, ligroin, benzene, toluene, xylene, chlorobenzene, petroleum ether, pentane, hexane, heptane, cyclohexane, methylene chloride, chloroform and carbon tetrachloride, ethers, such as diethyl ether, dioxane, tetrahydrofuran or ethylene glycol dimethyl or diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric acid triamide, or esters, such as ethyl acetate. The amines of the formula (IV) in liquid form can likewise be employed in a corresponding excess as the solvent.

If appropriate, process (c) according to the invention is carried out in the presence of a dehydrating agent. Dehydrating agents which are preferably used are alkali metal carbonates, such as, for example, potassium carbonate; molecular sieves or—in catalytic amounts—for example p-toluenesulphonic acid. Azeotropic removal of the water by distillation during the reaction represents a favourable procedure.

The reaction temperatures can be varied within a substantial range in carrying out process (c) according to the invention. The reaction is in general carried out at temperatures between 0° C. and 250° C., preferably at temperatures between 20° C. and 200° C.

Process (c) according to the invention is usually carried out under normal pressure. However, it is also possible for the process to be carried out under increased pressure.

For carrying out process (c) according to the invention, in general 1 to 10 moles, preferably 1 to 2.5 moles of amine of the formula (IV) and if appropriate 1 to 5 moles of dehydrating agent are employed per mole of compound of the formula (I) in which B represents hydroxyl. The reaction is carried out and the reaction products are worked up and isolated by a process analogous to generally known processes.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrstis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention are particularly suitable for selectively combating mono- and dicotyledon weeds in mono- and dicotyledon crops by the pre- and post-emergence method.

The compounds according to the invention moreover also exhibit an action as leaf insecticides.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foamforming agents there are suitable: for example non-ionic and anionic emulsifiers, such as polyoxyethylene fatty acid esters, polyoxyethylene fatty alcohol ethers, for example alkylaryl polyglycol ethers, alkylsulphoantes, alkyl sulphates, arylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For controlling weeds, the active compounds according to the invention, as such or in the form of their formulations, can also be used as mixtures with known herbicides, finished formulations or tank mixes being possible.

Possible components for the mixtures are known herbicides, such as, for example, aryloxy alkanoic acids, such as 2,4 D, 2,4 DP, 2,4-DB, MCPA, MCPP, fluoroxypyr, aryloxy-phenyl-alkanoic acid esters, such as diclofopmethyl, fenoxaprop, fluazifop-butyl, quizalofop, and haloxyfop, arylcarboxylic acids, such as clopyralid, azinones, such as chloridazon and norflurazon, carbamates, such as phenmedipham, propham, chlorpropham and asulam, chloroacetanilides, such as alachlor, butachlor, metazachlor, metolachlor, pretilachlor and propachlor, dinitroanilines, such as oryzalin, pendimethalin and trifluoralin, diphenyl ethers, such as acifluorfen, bifenox, fomesafen, lactofen and oxyfluorfen, ureas, such as chlortoluron, fluormeturon, isoproturon and methabenzthiazuron, hydroxylamines, such as alloxydim, cycloxydim and sethoxydim, imidazolinones, such as imazethapyr, imazamethabenz and imazaquin, nitriles, such as bromoxynil and ioxynil, oxyacetamides, such as mefenacet, sulphonylureas, such as bensulphuron, chlorimuron, chlorsulphuron, metasulphuron and thiameturon, thiobencarbamates, such as cycloate, EPTC, molinate, thiobencarb and triallate, triazinediones, such as amethydione, triazines, such as atrazine, cyanazine, simazine, simetryne and terbutryne, or triazines, such as ethiozin, hexazinon, metamitron or metribuzin, or other bentazons, cinmethylin, fluridone, glyphosate, pyridate and dimethazone. Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.001 and 10 kg of active compound per hectare of soil surface, preferably between 0.01 and 5 kg per ha.

The preparation and use of the active compounds according to the invention can be seen from the following examples.

PREPARATION EXAMPLES

Example 1

Process (a)

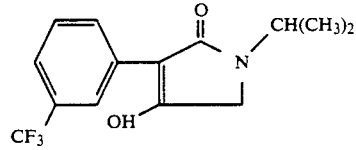

3-(3-Trifluoromethylphenyl)-1-isopropyl-pyrrolidine-2,4-dione 33.1 g (0.1 mol) of ethyl N-(3-trifluoromethylphenylacetyl)-N-isopropyl-aminoacetate in 100 ml of absolute toluene are added dropwise to 3.6 g (0.12 mol) of sodium hydride, 80% strength, in 55 ml of absolute toluene at 95° to 100° C. in the course of about 60 minutes. The mixture is then subsequently stirred at 100° C. for a further hour, and 30 ml of ethanol, and subsequently 80 ml of water, followed by 10 ml of concentrated hydrochloric acid, are then added dropwise, while cooling with an ice bath. The product which has precipitated is filtered off with suction, rinsed thoroughly first with water and then with petroleum ether and dried. Colourless crystals of the product are obtained: 51.1 g (78.2% of theory), melting point 207° to 208° C.

The end products of the formula (I), in which B represents hydroxyl, listed below in Table 1 are obtained in a manner analogous to Example 1 and taking into account the information in the description of process (a) according to the invention:

TABLE 1

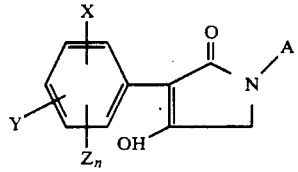
(Ia)

| Example No. | X | Y | $Z_n$ | A | Melting point °C. |
|---|---|---|---|---|---|
| 2 | 3-CF$_3$ | H | — | —C(CH$_3$)$_2$—CH$_2$—C(CH$_3$)$_3$ | 223 |

TABLE 1-continued
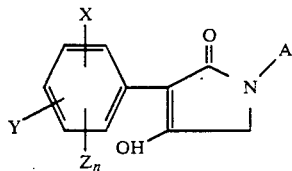
(Ia)
| Example No. | X | Y | $Z_n$ | A | Melting point °C. |
|---|---|---|---|---|---|
| 3 | 3-$CF_3$ | H | — | 2,4,6-trimethylphenyl | 248 |
| 4 | 3-$CF_3$ | H | — | cyclopropyl | 240 (Decomposition) |
| 5 | 3-$CF_3$ | H | — | cyclopentyl | 234 |
| 6 | 3-$CF_3$ | H | — | cyclohexyl | 245 |
| 7 | 3-$CF_3$ | H | — | —$CH_2CH_2$—O—$CH_3$ | 181 |
| 8 | 3-$CF_3$ | H | — | —CH($CF_3$)($CH_3$) | 184 |
| 9 | 3-$CF_3$ | H | — | phenyl | 244 (Decomposition) |
| 10 | 3-$CF_3$ | H | — | 2-chlorophenyl | 199 |
| 11 | 3-$CF_3$ | H | — | 4-chlorophenyl | 216 |
| 12 | 3-$CF_3$ | H | — | 2,4-dichlorophenyl | 108 |
| 13 | 3-$CF_3$ | H | — | 2,6-dichlorophenyl | 182 |

TABLE 1-continued
(Ia)
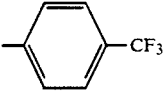
| Example No. | X | Y | Z$_n$ | A | Melting point °C. |
|---|---|---|---|---|---|
| 14 | 3-CF$_3$ | H | — | 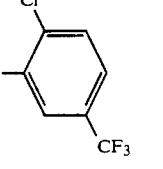 4-CF$_3$-phenyl | 224 |
| 15 | 3-CF$_3$ | H | — | 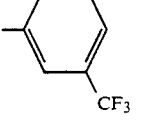 2-Cl-5-CF$_3$-phenyl | 189 |
| 16 | 3-CF$_3$ | H | — | 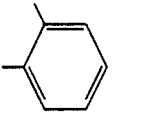 3-CF$_3$-phenyl | 208 |
| 17 | 3-CF$_3$ | H | — | 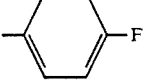 2-F-phenyl | 235 |
| 18 | 3-CF$_3$ | H | — | 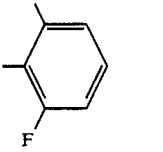 4-F-phenyl | 230 |
| 19 | 3-CF$_3$ | H | — | 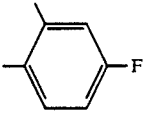 2,6-F$_2$-phenyl | Oil |
| 20 | 3-CF$_3$ | H | — | 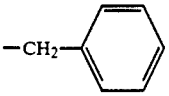 2,4-F$_2$-phenyl | 226 |
| 21 | 3-CF$_3$ | H | — | —CH$_2$—C(CH$_3$)$_3$ | 242 |
| 22 | 3-CF$_3$ | H | — | —CH(CH$_3$)—C(CH$_3$)$_3$ | 125 |
| 23 | 3-CF$_3$ | H | — | —CH$_2$— 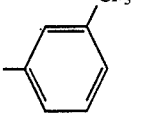 | 201 |
| 24 | H | H | — |  3-CF$_3$-phenyl | >250 |
| 25 | H | H | — | cyclopropyl | 238 (Decomposition) |

TABLE 1-continued
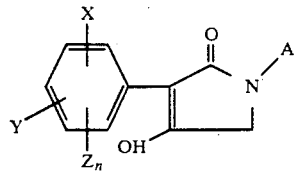
(Ia)
| Example No. | X | Y | $Z_n$ | A | Melting point °C. |
|---|---|---|---|---|---|
| 26 | 3-CF$_3$ | H | — | —CH(CH$_3$)—CH(CH$_3$)$_2$ | 193 |
| 27 | 3-CF$_3$ | H | — | 3,4-dichlorophenyl | 239 |
| 28 | 3-O-phenyl | 5-F | 2,4,6-Cl$_3$ | phenyl | 204 |
| 29 | 4-O-(3-F, 5-Cl, 4-CF$_3$)phenyl | H | — | phenyl | >250 |
| 30 | 3-CF$_3$ | H | — | 3-chlorophenyl | 227 |
| 31 | H | H | — | phenyl | >250 |
| 32 | H | H | — | 2,4-difluorophenyl | 226 |
| 33 | 2-O-(3-CH$_3$, 5-CH$_3$)phenyl | H | — | phenyl | 170 |
| 34 | 2-O-phenyl | H | — | phenyl | 234 |
| 35 | 3-CF$_3$ | H | — | 4-phenoxyphenyl | 231 |
| 36 | 3-CF$_3$ | H | — | 4-(4-CF$_3$-phenoxy)phenyl | 205 |

TABLE 1-continued (Ia)

[Structure: Phenyl ring with X, Y, Z_n substituents connected to a 5-membered ring containing OH and C(=O)-N(A)-CH2]

| Example No. | X | Y | Z_n | A | Melting point °C. |
|---|---|---|---|---|---|
| 37 | 2-O-(2-Cl,4-CF₃,6-F-phenyl) | H | — | phenyl | 222 |
| 38 | H | H | — | 2-Cl-phenyl | 102 |
| 39 | 2-F | 4-F | — | 3-CF₃-phenyl | 211 |
| 40 | 3-CF₃ | H | — | 3-CF₃-4-phenoxy-phenyl | Oil |
| 41 | H | H | — | 3-Cl-phenyl | 180 |
| 42 | H | H | — | 4-Cl-phenyl | >250 |
| 43 | H | H | — | 3,4-diCl-phenyl | 240 |
| 44 | 3-CF₃ | H | — | CH₃ | 260 |
| 45 | 3-CF₃ | H | — | C(CH₃)₃ | >230 |
| 46 | 3-O-phenyl | H | — | phenyl | 212–213 |
| 47 | 3-O-phenyl | H | — | 3-CF₃-phenyl | 160 |

TABLE 1-continued
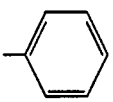
(Ia)
| Example No. | X | Y | $Z_n$ | A | Melting point °C. |
|---|---|---|---|---|---|
| 48 | 4-O-phenyl | H | — | phenyl | 226–227 |
| 49 | 4-O-phenyl | H | — | 3-CF$_3$-phenyl | 191 |
| 50 | 3-CF$_3$ | H | — | 4-cyclohexyl-phenyl | 237–238 |
| 51 | 2-O-phenyl | H | — | 3-CH$_3$-phenyl | 105 |
| 52 | H | H | — | 4-F-phenyl | >250 |
| 53 | 3-CF$_3$ | H | — | 2-CH$_3$-phenyl | 222–223 |
| 54 | 3-CF$_3$ | H | — | 3-CH$_3$-phenyl | 247–248 |
| 55 | 3-CF$_3$ | H | — | 4-CH$_3$-phenyl | >250 |
| 56 | 4-CH$_3$ | H | — | 4-F-phenyl | >250 |
| 57 | 2-CH$_3$ | H | — | 4-F-phenyl | 220–221 |

TABLE 1-continued
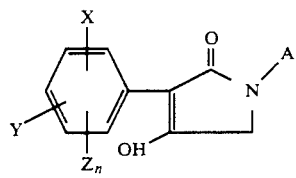
(Ia)
| Example No. | X | Y | $Z_n$ | A | Melting point °C. |
|---|---|---|---|---|---|
| 58 | 2-CH$_3$ | H | — | 3-CF$_3$-phenyl | oil |
| 59 | 2-F | H | — | 2-CH$_3$-phenyl | 236–237 |
| 60 | 4-F | H | — | 2-CH$_3$-phenyl | >250 |
| 61 | 2-F | H | — | 4-CH$_3$-phenyl | >250 |
| 62 | 2-F | H | — | 3-CF$_3$-phenyl | 209 |
| 63 | 4-F | H | — | phenyl | >250 |
| 64 | 4-F | H | — | 3-Cl-phenyl | 243–244 |
| 65 | 2,4-F$_2$ | H | — | 4-F-phenyl | 253–254 |
| 66 | 2,4-F$_2$ | H | — | 2-CH$_3$-phenyl | 174 |
| 67 | 2,4-F$_2$ | H | — | 3-CH$_3$-phenyl | 241 |

TABLE 1-continued (Ia)

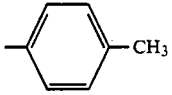

| Example No. | X | Y | $Z_n$ | A | Melting point °C. |
|---|---|---|---|---|---|
| 68 | 2,4-F$_2$ | H | — | 4-CH$_3$-phenyl | >250 |
| 69 | 2,4-F$_2$ | H | — | 2,4-F$_2$-phenyl | 210–211 |
| 70 | 3-F | H | — | 2-CH$_3$-phenyl | 247–248 |
| 71 | 3-F | H | — | 4-CH$_3$-phenyl | 249–250 |
| 72 | 3-F | H | — | 2-F-phenyl | 245–246 |
| 73 | 2-Me | H | — | phenyl | 186 |

EXAMPLE 41 a

Process (c)
3-(3-Trifluoromethylphenyl)-1-isopropyl-4-(N-methylamino)-3-pyrrolin-2-one

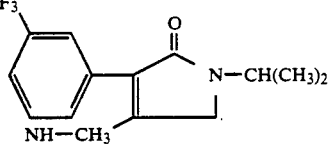

62.4 g of a 32% strength aqueous methylamine solution are added to a suspension of 28.5 g (0.1 mol) of 3-(3-trifluoromethylphenyl)-1-isopropyl-pyrrolidine-2,4-dione (prepared according to Example 1) in 500 ml of xylene to which 50 ml of glacial acetic acid have been added. The mixture is heated for 4 hours, using a water separator. It is then concentrated in vacuo, the crude product which remains is taken up in 300 ml of water, the mixture is extracted twice with 150 ml of methylene chloride each time and the combined extracts are concentrated in vacuo. The product which remains is stirred with petroleum ether, filtered off with suction and dried. 6.7 g (91% of theory) of the product (colorless crystals) are obtained, melting point: 161°–2° C.

The end products of the formula (I) in which B represents

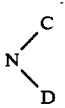

are obtained in an analogous manner to Example 41 and taking into account the information in the description of process (c) according to the invention.

TABLE 2
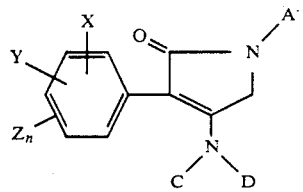
(Ib)
| Example No. | X | Y | $Z_n$ | A | C | D | Melting point °C. |
|---|---|---|---|---|---|---|---|
| 74 | 3-$CF_3$ | H | — | —C($CH_3$)$_2$—$CH_2$—C($CH_3$)$_3$ | H | $CH_3$ | 132 |
| 75 | 3-$CF_3$ | H | — | 2,4,6-trimethylphenyl | H | $CH_3$ | 194 |
| 76 | 3-$CF_3$ | H | — | cyclopropyl | H | $CH_3$ | 133 |
| 77 | 3-$CF_3$ | H | — | cyclopentyl | H | $CH_3$ | 177 |
| 78 | 3-$CF_3$ | H | — | cyclohexyl | H | $CH_3$ | 167 |
| 79 | 3-$CF_3$ | H | — | —$CH_2CH_2$—O—$CH_3$ | H | $CH_3$ | oil |
| 80 | 3-$CF_3$ | H | — | —CH(CH$_3$)(CF$_3$) | H | $CH_3$ | 147 |
| 81 | 3-$CF_3$ | H | — | phenyl | H | $CH_3$ | 163 |
| 82 | 3-$CF_3$ | H | — | 2-Cl-phenyl | H | $CH_3$ | 92 |
| 83 | 3-$CF_3$ | H | — | 4-Cl-phenyl | H | $CH_3$ | 154 |
| 84 | 3-$CF_3$ | H | — | 2,4-di-Cl-phenyl | H | $CH_3$ | 158 |
| 85 | 3-$CF_3$ | H | — | 2,6-di-Cl-phenyl | H | $CH_3$ | 156 |

TABLE 2-continued
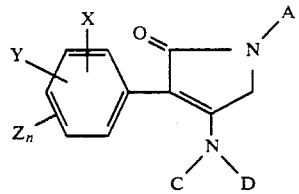
(Ib)
| Example No. | X | Y | $Z_n$ | A | C | D | Melting point °C. |
|---|---|---|---|---|---|---|---|
| 86 | 3-$CF_3$ | H | — | 4-$CF_3$-phenyl | H | $CH_3$ | 137 |
| 87 | 3-$CF_3$ | H | — | 2-Cl-5-$CF_3$-phenyl | H | $CH_3$ | 109 |
| 88 | 3-$CF_3$ | H | — | 3-$CF_3$-phenyl | H | $CH_3$ | 125 |
| 89 | 3-$CF_3$ | H | — | 2-F-phenyl | H | $CH_3$ | 115 |
| 90 | 3-$CF_3$ | H | — | 4-F-phenyl | H | $CH_3$ | 144 |
| 91 | 3-$CF_3$ | H | — | 2,6-diF-phenyl | H | $CH_3$ | 109 |
| 92 | 3-$CF_3$ | H | — | 2,4-diF-phenyl | H | $CH_3$ | 199 |
| 93 | 3-$CF_3$ | H | — | —$CH(CH_3)_2$ | H | H | 166 |
| 94 | 3-$CF_3$ | H | — | —$CH(CH_3)_2$ | H | —$CH(CH_3)_2$ | 162 |
| 95 | 3-$CF_3$ | H | — | —$CH_3$ | H | —$CH(CH_3)_2$ | 158 |
| 96 | 3-$CF_3$ | H | — | —$CH_2C(CH_3)_3$ | H | $CH_3$ | 168 |
| 97 | 3-$CF_3$ | H | — | —$CH(CH_3)$—$C(CH_3)_3$ | H | $CH_3$ | 135 |
| 98 | 3-$CF_3$ | H | — | —$CH_2$-phenyl | H | $CH_3$ | 75 |

TABLE 2-continued
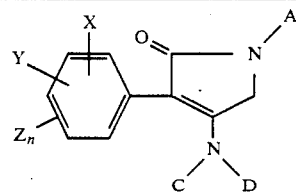
(Ib)
| Example No. | X | Y | $Z_n$ | A | C | D | Melting point °C. |
|---|---|---|---|---|---|---|---|
| 99 | H | H | — | 3-CF₃-phenyl | H | CH₃ | 141 |
| 100 | 3-CF₃ | H | — | —CH(CH₃)₂ | H | phenyl | 188 (decomp.) |
| 101 | 3-CF₃ | H | — | cyclopropyl | H | phenyl | 186 |
| 102 | 3-CF₃ | H | — | phenyl | H | phenyl | 194 (decomp.) |
| 103 | H | H | — | cyclopropyl | H | 3-CF₃-phenyl | 183 |
| 104 | 3-CF₃ | H | — | —CH(CH₃)—C(CH₃)₃ | H | CH₃ | 118 |
| 105 | 3-CF₃ | H | — | cyclopropyl | H | H | 151 |
| 106 | 3-CF₃ | H | — | 3,4-Cl₂-phenyl | H | CH₃ | 183 |
| 107 | 3-CF₃ | H | — | cyclopropyl | H | 4-Cl-phenyl | 190 |
| 108 | 3-O-phenyl | 5-F | 2,4,6-Cl₃ | phenyl | H | CH₃ | 110 |
| 109 | 3-O-phenyl | 5-F | 2,4,6-Cl₃ | phenyl | H | phenyl | 115 |
| 110 | 3-CF₃ | H | — | 3-Cl-phenyl | H | CH₃ | 153 |

TABLE 2-continued (Ib)

| Example No. | X | Y | Z$_n$ | A | C | D | Melting point °C. |
|---|---|---|---|---|---|---|---|
| 111 | 3-CF$_3$ | H | — | 2,4-difluorophenyl | H | C$_2$H$_5$ | 124 |
| 112 | H | H | — | phenyl | H | 3-(trifluoromethyl)phenyl | 134 |
| 113 | H | H | — | 2,4-difluorophenyl | H | CH$_3$ | 161 |
| 114 | H | H | — | 3-(trifluoromethyl)phenyl | H | 2,4-difluorophenyl | >250 |
| 115 | 3-CF$_3$ | H | — | 2,4-difluorophenyl | \multicolumn{2}{l|}{tetrahydropyran-yl} | 188 |
| 116 | 3-CF$_3$ | H | — | 2,4-difluorophenyl | \multicolumn{2}{l|}{di(sec-butyl)} | 180 |
| 117 | 3-CF$_3$ | H | — | 2,4-difluorophenyl | \multicolumn{2}{l|}{piperidinyl} | 151 |
| 118 | 3-CF$_3$ | H | — | 2,4-difluorophenyl | \multicolumn{2}{l|}{4-acetylpiperazinyl} | >250 |
| 119 | 3-CF$_3$ | H | — | cyclopropyl | \multicolumn{2}{l|}{2,6-dimethyltetrahydropyran-yl} | 102 |

TABLE 2-continued
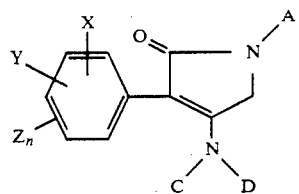
(Ib)
| Example No. | X | Y | $Z_n$ | A | C | D | Melting point °C. |
|---|---|---|---|---|---|---|---|
| 120 | 3-CF$_3$ | H | — | cyclopropyl | morpholino (O) | | 93 |
| 121 | 3-CF$_3$ | H | — | cyclopropyl | piperazinyl N—COCH$_3$ | | 43 |
| 122 | 3-CF$_3$ | H | — | cyclopropyl | cyclopentyl | | 108 |
| 123 | 3-CF$_3$ | H | — | cyclopropyl | piperidino | | 92 |
| 124 | 2-O-phenyl | H | — | phenyl | H | CH$_3$ | 149 |
| 125 | 3-CF$_3$ | H | — | 2,4-difluorophenyl | cyclopentenyl | | 115 |
| 126 | H | H | — | phenyl | H | CH$_3$ | 178 |
| 127 | 3-CF$_3$ | H | — | 4-phenoxyphenyl | H | CH$_3$ | Oil |
| 128 | 2-Cl, 5-CF$_3$, 4-F | H | — | phenyl | H | CH$_3$ | 190 |
| 129 | 2-F | 4-F | — | 3-CF$_3$-phenyl | H | CH$_3$ | 168 |

TABLE 2-continued
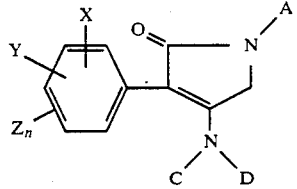
(Ib)
| Example No. | X | Y | $Z_n$ | A | C | D | Melting point °C. |
|---|---|---|---|---|---|---|---|
| 130 | 3-CF$_3$ | H | — | 4-(4-CF$_3$-phenoxy)phenyl | H | CH$_3$ | Oil |
| 131 | H | H | — | 3-Cl-phenyl | H | CH$_3$ | 157 |
| 132 | H | H | — | phenyl | H | CH$_3$ | 188 |
| 133 | H | H | — | 3,4-diCl-phenyl | H | CH$_3$ | 152 |
| 134 | 3-O-phenyl | H | — | phenyl | H | CH$_3$ | 203 |
| 135 | 3-O-phenyl | H | — | 3-CF$_3$-phenyl | H | CH$_3$ | 166 |
| 136 | 3-CF$_3$ | H | — | CH$_3$ | H | H | 167 |
| 137 | 3-CF$_3$ | H | — | 4-cyclohexyl-phenyl | H | CH$_3$ | 142 |
| 138 | 2-O-phenyl | H | — | 3-CF$_3$-phenyl | H | CH$_3$ | 160 |
| 139 | H | H | — | 4-F-phenyl | H | CH$_3$ | 196 |
| 140 | 3-CF$_3$ | H | — | 3-CH$_3$-phenyl | H | CH$_3$ | 128 |

TABLE 2-continued
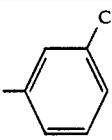
(Ib)
| Example No. | X | Y | $Z_n$ | A | C | D | Melting point °C. |
|---|---|---|---|---|---|---|---|
| 141 | 3-CF$_3$ | H | — | 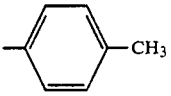 3-CH$_3$-phenyl | H | CH$_3$ | 67 |
| 142 | 3-CF$_3$ | H | — | 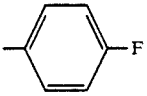 4-CH$_3$-phenyl | H | CH$_3$ | 194 |
| 143 | 4-CH$_3$ | H | — | 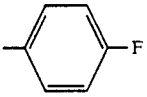 4-F-phenyl | H | CH$_3$ | 189 |
| 144 | 2-CH$_3$ | H | — | 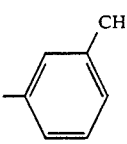 4-F-phenyl | H | CH$_3$ | 246–247 |
| 145 | 2-CH$_3$ | H | — | 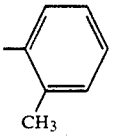 3-CH$_3$-phenyl | H | CH$_3$ | 152 |
| 146 | 3-F | H | — | 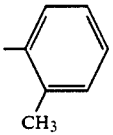 2-CH$_3$-phenyl | H | CH$_3$ | 190 |
| 147 | 4-F | H | — | 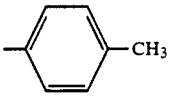 2-CH$_3$-phenyl | H | CH$_3$ | 131 |
| 148 | 2-F | H | — | 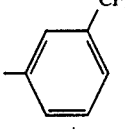 4-CH$_3$-phenyl | H | CH$_3$ | 242–243 |
| 149 | 2-F | H | — | 3-CF$_3$-phenyl | H | CH$_3$ | 139 |
| 150 | 4-F | H | — | 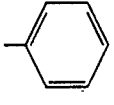 phenyl | H | CH$_3$ | 146 |

TABLE 2-continued

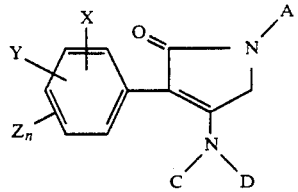

(Ib)

| Example No. | X | Y | $Z_n$ | A | C | D | Melting point °C. |
|---|---|---|---|---|---|---|---|
| 151 | 2,4-F$_2$ | H | — | 4-F-C$_6$H$_4$ | H | CH$_3$ | 198 |
| 152 | 2,4-F$_2$ | H | — | 2-CH$_3$-C$_6$H$_4$ | H | CH$_3$ | 184 |
| 153 | 2,4-F$_2$ | H | — | 3-CH$_3$-C$_6$H$_4$ | H | CH$_3$ | 214–215 |
| 154 | 2,4-F$_2$ | H | — | 4-CH$_3$-C$_6$H$_4$ | H | CH$_3$ | 230–231 |
| 155 | 2-CH$_3$ | H | — | C$_6$H$_5$ | H | CH$_3$ | 234 |

EXAMPLE 156

Process (b)

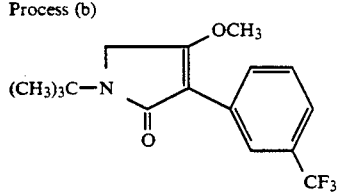

3-(3-Trifluoromethylphenyl)-1-tert.butyl-4-methoxy-3-pyrrolin-2-one 3.89 (13 mmol) of 3-(3-trifluoromethylphenyl)-1-tert.-butyl-pyrrolidine-2,4-dione are suspended in 30 ml of absolute acetonitrile and, after addition of 0.84 g (15 mmol) of powdered potassium hydroxide and 2.8 g (15 mmol) of methyl p-toluenesulphonate, dissolved in 5 ml of absolute acetonitrile, the mixture is refluxed for 3 hours. It is stirred into 200 ml of water and extracted with methylene chloride and the extract is dried and concentrated. The residue is purified by column chromatography on silica gel using cyclohexane/ethyl acetate 1:2.

Crystallization from ether/n-hexane gives 2.03 g (47.2% of theory) of 3-(3-trifluoromethylphenyl)-1-tert.-butyl-4-methoxy-3-pyrrolin-2-one of melting point 129° C.

The following compound is obtained analogously:

EXAMPLE 157

3-(3-Trifluoromethylphenyl)-1-(2-methoxyethyl)-4-methoxy-3-pyrrolin-2-one in a yield of 56.2% as an oil.

USE EXAMPLES

Example A

Post-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)

100% = total destruction

In this test, compounds 82, 89 and 92 exhibit a very good herbicidal action against dicotyledon weeds, coupled with a very good tolerance towards crop plants, such as, for example, in cotton, wheat or barley.

EXAMPLE B

Pre-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, compounds 81, 88, 89 and 92 exhibit a very good herbicidal action against mono- and dicotyledon weeds coupled with an excellent tolerance towards crop plants, such as, for example, in barley, corn, soya or cotton.

It is understood that the specification and examples are illustrative but not limitative of the present invention and that other embodiments within the spirit and scope of the invention will suggest themselves to those skilled in the art.

We claim:

1. A 4-alkoxy- or 4-(substituted) amino-3-aryl-pyrrolinone of the formula

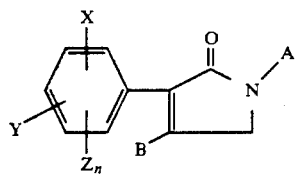

in which
X and Y independently of one another represent hydrogen, fluorine, chlorine, bromine, iodine, $C_1-C_6$-alkyl, $C_1-C_6$-alkoxy, halogeno-$C_1-C_4$-alkyl or phenoxy or phenylthio which are in each case unsubstituted or substituted by one to five identical or different substituents, the substituents on the phenyl being fluorine, chlorine, bromine, iodine, $C_1-C_4$-alkyl, $C_1-C_4$-alkoxy or halogen-$C_1-C_4$-alkyl, Z represents fluorine, chlorine, bromine, iodine, $C_1-C_6$-alkyl or $C_1-C_6$-alkoxy, n represents the number 0, 1, 2 or 3, A represents in each case unsubstituted or in each case halogen-substituted $C_1-C_{12}$-alkyl, $C_3-C_8$-alkenyl, $C_3-C_8$-alkynyl, $C_1-C_{10}$-alkoxy-$C_2-C_8$-alkyl, $C_1-C_8$-polyalkoxy-$C_1-C_8$-alkyl or $C_1-C_{10}$-alkylthio-$C_1-C_8$-alkyl, or represents cycloalkyl which has 3 to 8 ring atoms and can be interrupted by one nitrogen atom to form a four or five membered ring or by oxygen and/or sulphur, or A represents phenyl-$C_1-C_6$-alkyl, phenyl or naphthyl, in each case unsubstituted or substituted in the phenyl part by one to five identical or different substituents selected from the group consisting of fluorine, chlorine, bromine, iodine, $C_1-C_6$-alkyl, $C_1-C_6$-alkoxy, halogeno-$C_1-C_6$-alkyl, halogeno-$C_1-C_6$-alkoxy and phenoxy or phenylthio which are in each case unsubstituted or substituted by one to five identical or different substituents from the group consisting of fluorine, chlorine, bromine, iodine, $C_1-C_4$-alkyl, $C_1-C_4$-alkoxy, halogeno-$C_1-C_4$-alkyl and halogeno-$C_1-C_4$-alkoxy, represents hydroxyl, $C_1-C_{10}$-alkoxy, halogeno-$C_1-C_{10}$-alkoxy or cycloalkoxy having 3 to 7 ring atoms, the cycloalkyl radical being unsubstituted or substituted by one to five identical or different substituents from the group consisting of fluorine, chlorine, bromine and $C_1-C_4$-alkyl, or represents the group

wherein
C and D independently of one another represent hydrogen, $C_1-C_{10}$-alkyl, $C_3-C_{10}$-alkenyl, $C_1-C_8$-alkoxy-$C_1-C_8$-alkyl, $C_1-C_8$-alkylthio-$C_1-C_8$-alkyl, $C_1-C_8$-polyalkoxy-$C_1-C_8$-alkyl, cycloalkyl having 3 to 8 ring atoms, which can be interrupted by one nitrogen atom to form a four or five membered ring or by one, two or three oxygen or sulphur atoms, or phenyl, phenyl-$C_1-C_6$-alkyl, phenoxy-$C_1-C_6$-alkyl, hetaryl or hetaryl-$C_1-C_6$-alkyl, having in each case 5 or 6 ring atoms and containing one nitrogen atom to form a pyrrolidinyl ring or 1 or 2 oxygen or sulphur atoms in the ring, which are in each case unsubstituted or substituted by one to five identical or different substituents, or C and D, together with the nitrogen atom to which they are bonded, represents a heterocyclic radical of the formula:

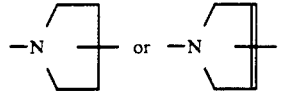

which is optionally substituted by one to five identical or different substituents from the group consisting of $C_1-C_4$-alkyl and $C_1-C_4$-alkylcarbonyl, with the proviso that at least one radical X, Y or Z does not represent chlorine or methyl if B represents hydroxyl and A has a meaning other than optionally substituted phenyl or naphthyl excluding the compound wherein B=hydroxy; X, Y and Z=hydrogen and A=2,6-diethyl phenyl.

2. A 4-alkoxy- or 4(substituted) amino-3-arylpyrrolinone according to claim 1, in which B represents hydroxyl, methoxy, ethoxy, n- or isopropoxy, n-, iso-, sec.- or tert.-butoxy, halogeno-$C_1-C_4$-alkoxy, containing fluorine and/or chlorine atoms, or cycloalkoxy having 3 to 6 ring atoms, the cycloalkyl radical being unsubstituted or substituted by one to three identical or different substituents from the group consisting of fluorine, chlorine, methyl and ethyl, X represents hydrogen, fluorine, chlorine, methyl, ethyl, n- or iso-propyl, methoxy, ethoxy, n- or i-propoxy, halogenomethyl, containing 1, 2 or 3 fluorine and/or chlorine atoms, halogenoethyl, containing 1 to 5, in particular 1 to 3, fluorine and/or chlorine atoms, or phenoxy or phenylthio which are in each case unsubstituted or substituted by one to five identical or different substituents selected from the group consisting of fluorine, chlorine, bromine, methyl, ethyl, n- or iso-propyl, methoxy, ethoxy, n- or iso-propoxy and trifluoromethyl, Y represents hydrogen, fluorine, chlorine, methyl, ethyl, methoxy, ethoxy or trifluoromethyl, Z represents fluorine or chlorine, n represents 0, 1, 2 or 3 and A represents methyl, ethyl, in each case straight-chain or branched propyl, butyl, pentyl, hexyl, heptyl, octyl, nonyl or decyl, halogeno-$C_1$-$C_6$-alkyl, $C_3$-$C_6$-alkenyl, $C_3$-$C_6$-alkynyl, $C_1$-$C_4$-alkoxy-$C_1$-$C_4$-alkyl or $C_1$-$C_4$-alkylthio-$C_1$-$C_4$-alkyl, or represents cycloalkyl which has 3 to 6 ring atoms and can be interrupted one nitrogen atoms or by oxygen, or sulphur, or A represents phenyl, benzyl or phenethyl which are in each case unsubstituted or substituted by one to five identical or different substituents selected from the group consisting of fluorine, chlorine, methyl, ethyl n- or iso-propyl, methoxy, ethoxy, trifluoromethyl, trifluoromethoxy and phenoxy or phenylthio, which are in each case unsubstituted or substituted by one to three identical or different substituents from the group consisting of fluorine, chlorine, methyl, methoxy, trifluoromethyl and trifluoromethoxy, with the proviso that at least one radical X, Y or Z does not represent chlorine or methyl if B represents hydroxyl and A has a meaning other than optionally substituted phenyl.

3. A 4-alkoxy- or 4-(substituted) amino-3-aryl-pyrrolinone according to claim 1, in which B represents the group

wherein

C represents hydrogen, methyl, ethyl or n- or iso-propyl and

D represents methyl, ethyl, n- or iso-propyl, n-, iso- sec.-or tert.-butyl, allyl, propargyl, methoxymethyl, methoxyethyl, ethoxymethyl, ethoxyethyl, methylthiomethyl, methylthioethyl, ethylthiomethyl, ethylthioethyl, cyclopropyl, cyclopentyl, cyclohexyl or phenyl, benzyl or phenethyl, which are in each case unsubstituted or substituted by one to five identical or different substituents from the group consisting of fluorine, chlorine, methyl, ethyl and trifluoromethyl, or C and D, together with the nitrogen atom to which they are bonded, represent a heterocyclic radical of the formula:

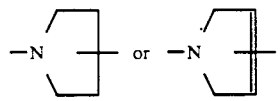

which is optionally substituted by one to three identical or different substituents from the group consisting of methyl, ethyl, methylcarbonyl and ethylcarbonyl, X represents hydrogen, fluorine, chlorine, methyl, ethyl, n- or iso-propyl, methoxy, ethoxy, n- or i-propoxy, halogenomethyl, which contains 1, 2 or 3 fluorine and/or chlorine atoms, halogenoethyl, which contains 1 to 5 fluorine and/or chlorine atoms, or phenoxy or phenylthio which are in each case unsubstituted or substituted by one to five identical or different substituents selected from the group consisting of fluorine, chlorine, bromine, methyl, ethyl, n- or iso-propyl, methoxy, ethoxy, n-or iso-propoxy and trifluoromethyl, Y represents hydrogen, fluorine, chlorine, methyl, ethyl, methoxy, ethoxy or trifluoromethyl, Z represents fluorine or chlorine, n represents 0, 1, 2 or 3 and A represents methyl, ethyl, in each case straight-chain or branched propyl, butyl, pentyl, hexyl, heptyl, octyl, nonyl or decyl, halogeno-$C_1$-$C_6$-alkyl, $C_3$-$C_6$-alkenyl, $C_3$-$C_6$-alkynyl, $C_1$-$C_4$-alkoxy-$C_1$-$C_4$-alkyl or $C_1$-$C_4$-alkylthio-$C_1$-$C_4$-alkyl, or represents cycloalkyl which has 3 to 6 ring atoms and can be interrupted by oxygen, nitrogen or sulphur, or A represents phenyl, benzyl or phenethyl, in each case unsubstituted or substituted by one to five identical or different substituents selected from the group consisting of fluorine, chlorine, methyl, ethyl, n- or iso-propyl, methoxy, ethoxy, trifluoromethyl, trifluoromethoxy and phenoxy or phenylthio, which are in each case unsubstituted or substituted by one to three identical or different substituents from the group consisting of fluorine, chlorine, methyl, methoxy, trifluoromethyl and trifluoromethoxy.

4. A compound according to claim 1, wherein

B represents hydroxyl, methoxy, ethoxy or n- or iso-proxy,

X represents fluorine, chlorine or trifluoromethyl in the meta-position of the phenyl ring, or represents phenyl or phenoxy, which are in each case unsubstituted or substituted by one to three identical or different substituents selected from the group consisting of fluorine, chlorine, methyl and trifluoromethyl, Y represents hydrogen, fluorine or chlorine, n represents 0 and A represents methyl, ethyl, n-propyl, iso-propyl, n-, iso-, sec.- or tert.-butyl, in each case straight-chain or branched pentyl, hexyl, heptyl or octyl, halogen-$C_1$-$C_3$-alkyl, allyl, propargyl, methoxymethyl, methoxyethyl, ethoxymethyl, ethoxyethyl, cyclopropyl, cyclopentyl, cyclohexyl, or phenyl or benzyl, which are in each case unsubstituted or substituted by one to three identical or different substituents from the group consisting of fluorine, chlorine, trifluoromethyl, phenoxy and 4-trifluoromethylphenoxy.

5. A compound according to claim 1, in which

B represents the group

wherein

C represents hydrogen and

D represents methyl, ethyl, n- or iso-propyl, n-, iso-, sec.- or tert.butyl or phenyl, which is unsubstituted or substituted by one to three identical or different substituents from the group consisting of fluorine, chlorine and trifluoromethyl, or C and D, together with the nitrogen to which they are bonded, represent a heterocyclic radical of the

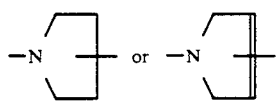

which is optionally substituted by one to three identical or different substituents from the group consisting of methyl, ethyl, methylcarbonyl and ethylcarbonyl, X represents fluorine, chlorine or trifluoromethyl in the meta-position of the phenyl ring, or represents phenyl or phenoxy, in each case unsubstituted or substituted by one to three identical or different substituents selected from the group consisting of fluorine, chlorine, methyl and trifluoromethyl, Y represents hydrogen, fluorine or chlorine, n represents 0 and A represents methyl, ethyl, n-propyl, isopropyl, n-, iso-, sec.- or tert.-butyl, in each case straight-chain or branched pentyl, hexyl, heptyl or octyl, halogen-$C_1$–$C_3$-alkyl, allyl, propargyl, methoxymethyl, methoxyethyl, ethoxymethyl, ethoxyethyl, cyclopropyl, cyclopentyl, cyclohexyl, or phenyl or benzyl which are in each case unsubstituted or substituted by one to three identical or different substituents from the group consisting of fluorine, chlorine, trifluoromethyl, phenoxy and 4-trifluoromethylphenoxy.

6. A compound according to claim 1, wherein such compound is 3-(3-trifluoromethylphenyl)-1-phenyl-4-(N-methyl-amino)-3-pyrrolin-2-one of the formula

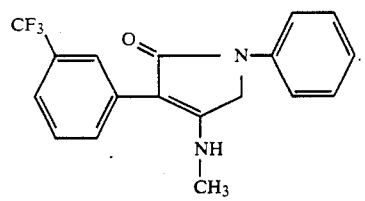

7. A compound according to claim 1, wherein such compound is 3-(3-trifluoromethylphenyl)-1-(2-chlorophenyl)-4-(N-methyl-amino)-3-pyrrolin-2-one of the formula

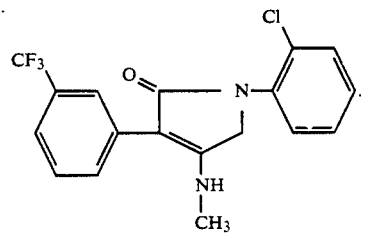

8. A compound according to claim 1, wherein such compound is 3-(3-trifluoromethylphenyl)-1-(2,6-difluorophenyl)-4-(N-methyl-amino)-3-pyrrolin-2-one of the formula

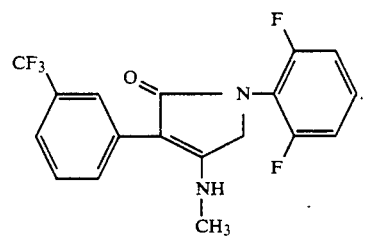

9. A compound according to claim 1, wherein such compound is 3-(2-chloro-6-fluoro-4-trifluoromethylphenyl)-1-phenyl-4-(N-methyl-amino)-3-pyrrolin-2-one of the formula

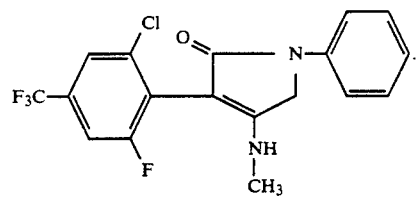

10. A compound according to claim 1, wherein such compound is 3-phenyl-1-(4-fluorophenyl)-4-(N-methyl-amino)-3-pyrrolin-2-one of the formula

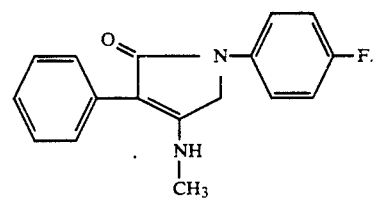

* * * * *

UNITED STATES PATENT AND TRADEMARK OFFICE
CERTIFICATE OF CORRECTION

PATENT NO. : 5,191,089

DATED : March 2, 1993

INVENTOR(S) : Baasner et al.

It is certified that error appears in the above-identified patent and that said Letters Patent is hereby corrected as shown below:

Col 48, lines 15-16   Before " represents " insert -- B --

Col. 48, line 22   Before " represents " insert -- B --

Signed and Sealed this

Twenty-sixth Day of July, 1994

Attest:

BRUCE LEHMAN

*Attesting Officer*   Commissioner of Patents and Trademarks